United States Patent
Meitzner

(10) Patent No.: US 8,263,812 B2
(45) Date of Patent: Sep. 11, 2012

(54) METHODS FOR DISPERSAL OF CATALYST PROMOTERS

(75) Inventor: George Meitzner, Aurora, CO (US)

(73) Assignee: Albemarle Corporation, Baton Rouge, LA (US)

( * ) Notice: Subject to any disclaimer, the term of this patent is extended or adjusted under 35 U.S.C. 154(b) by 509 days.

(21) Appl. No.: 12/505,160

(22) Filed: Jul. 17, 2009

(65) Prior Publication Data

US 2010/0022806 A1 Jan. 28, 2010

Related U.S. Application Data

(60) Provisional application No. 61/083,006, filed on Jul. 23, 2008.

(51) Int. Cl.
*C07C 31/08* (2006.01)
*B01J 21/18* (2006.01)
*B01J 27/02* (2006.01)
*B01J 27/51* (2006.01)

(52) U.S. Cl. .......... 568/840; 502/216; 502/220
(58) Field of Classification Search .......... 568/840; 502/216, 220
See application file for complete search history.

(56) References Cited

OTHER PUBLICATIONS

Yue Zong et al., "Dispersion State and Dispersion Capacity of AlCl3 and FeCl3 on γ-Al2O3 Surface", Cuihua Xuebao 18(4), 321-323 (1997).

*Primary Examiner* — Sikarl Witherspoon
(74) *Attorney, Agent, or Firm* — Jeremy J. Kliebert; Marcy M. Hoefling; James A. Jubinsky

(57) ABSTRACT

The present invention describes improved methods of introducing promoters to catalysts. This invention provides a method for dispersal of a promoter onto a solid surface. A catalyst material and a deliquescent material can together be contacted with a gas phase comprising a solvent under conditions effective for deliquescence whereby the promoter is dispersed onto the solid surface. This invention combines practical benefits of dry-mixing with the enhanced dispersion that can be realized by solvent-based methods.

22 Claims, 3 Drawing Sheets

METHODS FOR DISPERSAL OF CATALYST PROMOTERS

PRIORITY DATA

This patent application claims priority under 35 U.S.C. §120 from U.S. Provisional Patent Application No. 61/083,006 for "METHODS FOR DISPERSAL OF CATALYST PROMOTERS," the disclosure of which is hereby incorporated by reference herein for all purposes.

FIELD OF THE INVENTION

The present invention generally relates to the field of heterogeneous catalysts, and more specifically to methods of adding promoters to these catalysts.

BACKGROUND OF THE INVENTION

One of the steps commonly required for the synthesis of a heterogeneous catalyst involves the deposition of a component generically known as a "promoter," which might be an anionic, cationic, or molecular species, onto a surface of a catalytic material. The deposition process is usually intended to disperse the promoter broadly and uniformly.

The promoter is sometimes deposited out of the gas phase, as for example when HCl carried by an inert gas is reacted with a metal oxide, or when a metal is introduced by vaporizing its volatile carbonyl compounds into a carrier gas and decomposing the metal carbonyl onto the surface of a catalyst precursor.

In some situations a promoter that is ionic is deposited onto a catalyst precursor from solution in a polar solvent by ion exchange. This process requires that the catalyst precursor carry ionic groups on its surface so that a species that is usually a surface cation can be exchanged by a different cation out of a concentrated solution. This process is employed, for example, when a zeolite bearing oxide anions bound to the zeolite framework and neutralized by sodium countercations is converted to the acid form with proton countercations by exchange with aqueous ammonium cations followed by calcination to drive off ammonia.

Adsorption is a related process wherein a catalyst precursor extracts the promoter out of solution. Van der Waals forces can attach the promoter to the catalyst precursor (no exchangeable ions are involved).

Another common method for introducing a promoter onto a catalyst precursor involves dissolving a promoter in a solvent that may be water or some other fluid, and then depositing the promoter from the solution by evaporating the solvent. If the volume of solvent involved is about equal to the catalyst precursor pore volume, then the procedure is called "incipient wetness impregnation." Alternately, the catalyst precursor can be stirred with an excess volume of solution and the slurry evaporated to dryness so that the promoter originally in solution is deposited onto the catalyst surface. If enough solvent is used to cause the catalyst precursor to be conspicuously wetted, then the procedure is known as "solvent impregnation."

Finally, a promoter is sometimes added by dry-mixing the promoter and catalyst precursor solids and allowing the promoter to migrate to the catalyst surface as it is melted, volatilized, or otherwise rendered mobile inside the catalytic reactor in the presence of heat, reactants, and products.

Each of these procedures has limitations. Promoter deposition from the gas phase requires that the promoter have a volatile form. The ion-exchange method requires that both the catalyst precursor and the promoter be ionic, and further that the ion-exchange sites be the desired destination for the promoter. Adsorption forces may not be sufficiently strong. The deposition of a promoter from excess solvent by impregnation can lead to surface chemistry that may not be beneficial.

In the dry-mix approach, there is little or no control over the delivery of the promoter to the catalyst surface. In situ dispersal of a promoter that has been dry-mixed requires an induction period during which the catalyst is not effectively promoted.

In view of these limitations, improved methods of introducing promoters to catalysts are needed. Specifically, there is a need for practical methods to disperse promoters onto the surface of catalysts or catalyst precursors, wherein the dispersion leads to a substantially uniform promoter composition and efficient use of the promoter.

While solvent impregnation can give good promoter dispersion, there is a desire to minimize the use of solvents for several reasons: (i) potential damage to the catalyst by solvent contact is minimized, (ii) energy needs for later solvent removal are reduced, and (iii) waste solvent streams are minimized. It would be particularly advantageous to combine the practical benefits of dry-mixing a promoter and catalyst precursor, with the enhanced dispersion that can be realized by solvent-based methods.

SUMMARY OF THE INVENTION

The present invention addresses the aforementioned limitations in the catalyst-promoter art, at least in part, by combining certain aspects of both dry-mix and solvent-impregnation methods.

In some embodiments, the invention provides a method for dispersal of a promoter onto a solid surface, the method comprising:

(i) providing a catalyst material comprising a solid surface that is at least partially hydrophilic;

(ii) providing a deliquescent material comprising, in free or combined form, a promoter;

(iii) mixing the catalyst material and the deliquescent material, thereby creating a mixture; and (iv) contacting the mixture with a gas phase comprising a solvent, under conditions effective for deliquescence, whereby the promoter is dispersed onto the solid surface.

The solvent can be polar, such as water, DMF, a $C_1$-$C_3$ alcohol, a liquid amine, or a polar aprotic solvent. The solvent can be non-polar, such as a hydrocarbon, an ether, or a halocarbon. The solvent can optionally contain several chemicals. The gas phase can comprise an inert gas, air, or another gas mixture. The gas may be reactive, so that the promoter dispersal step is combined with another desired reactive step in the synthesis of the active catalyst.

The method is preferably conducted at a suitable temperature such that the solvent is condensable. The method is preferably conducted such that the promoter dispersal is substantially uniform.

In certain embodiments, the deliquescent material is $K_2CO_3$ and the promoter is potassium. In some embodiments, the catalyst material comprises a non-polar material selected from the group consisting of organic polymers, elemental carbon, and transition metal sulfides. In preferred embodiments, the solid surface has catalytic activity, and the promoter enhances the catalytic activity. The catalyst material can comprise cobalt, molybdenum, and sulfur. In certain embodiments, the catalytic activity causes the conversion of syngas into a mixture comprising one or more $C_1$-$C_4$ alcohols, such as ethanol. However, the invention is not limited to any particular reactant, product, or mechanism of catalysis.

The invention further includes, in some embodiments, the step of loading a material or mixture obtained from any of steps (i)-(iv) into a reactor. The promoter can be dispersed before the catalyst is loaded into the reactor.

In another variation of the invention, an apparatus is provided, wherein the apparatus is capable of carrying out the methods described herein.

DETAILED DESCRIPTION OF EMBODIMENTS OF THE INVENTION

Figure 1:
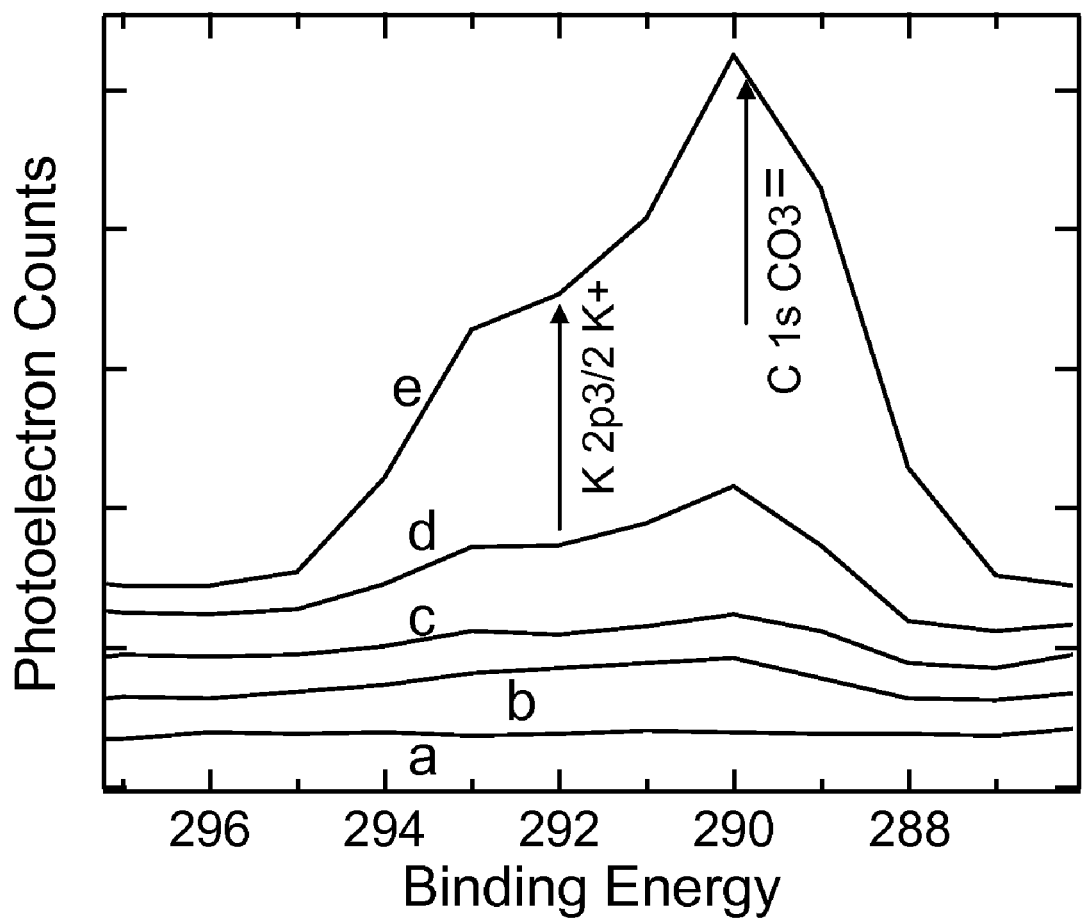
FIG. 1 shows XPS measurements of catalyst precursors mixed with $K_2CO_3$ at various stages of deliquescence.

This description will enable one skilled in the art to make and use the invention, and it describes several embodiments, adaptations, variations, alternatives, and uses of the invention, including what is presently believed to be the best mode of carrying out the invention.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in their respective testing measurements.

The present invention will now be described by reference to the following detailed description and accompanying drawings which characterize and illustrate some preferred embodiments for producing ethanol. This description by no means limits the scope and spirit of the present invention.

For the present purposes, "deliquescence" means conversion of a solid substance into a liquid solution as a result of absorption of solvent vapor (e.g., water vapor) from an ambient environment (e.g., air). With reference to water, for example, deliquescence can occur when the vapor pressure of the solution that is formed is less than the partial pressure of water vapor in the air.

As used herein, "$C_1$-$C_4$ alcohols" means one or more alcohols selected from methanol, ethanol, propanol, and butanol, including all known isomers of such compounds. While preferred embodiments are described in relation to high selectivities to ethanol, the invention can also be practiced in a manner that gives high selectivities to propanol and/or butanol, or certain combinations of selectivities to ethanol, propanol, and butanol, depending on the desired fuel attributes.

In some embodiments of the present invention, a promoter can be delivered to a catalyst from a dry solid compound that possesses the property of deliquescence. Specifically, the dry solid compound preferably absorbs water (or another solvent) from humid gas such that, if left exposed to ambient air, it rapidly collects enough solvent to become a liquid solution (a "puddle").

In order for a dissolved promoter to spread, the catalyst precursor should have a surface that is hydrophilic, meaning that the contact angle between water and the catalyst surface is between 0° and 90°, referred to as the condition of wetting. When this condition is met, then an aqueous (or solvent) solution should spontaneously spread across the solid surface to maximize the area of contact. The dispersal will generally be broader and more rapid when the contact angle between the solvent, such as water, and the solid surface is nearer to 0° than to 90°. This condition is satisfied by many inorganic solids commonly employed in catalysts, including, for example, Co—Mo—S and related materials.

In certain embodiments, dispersal of a promoter is accomplished by passing humidified carrier gas through a mixture of the catalyst precursor and promoter salt. This mixture can be contained in various configurations, including fixed beds, tumbled beds, or fluidized beds.

"Humidified carrier gas" means a gas phase comprising an appropriate solvent, which can be water or some other solvent. Specifically, the gas phase carries the vapor of a solvent. The gas is preferably one that is inert toward the catalyst precursor and the mechanical apparatus under the conditions for the procedure; preferred gases include nitrogen, argon, helium and the like, and may also be or include air. Alternatively, the gas may be reactive toward the catalyst so that a desired chemical reaction is combined into the precursor dispersal procedure. In this case the gas may include hydrogen, oxygen, hydrogen sulfide, or another reactive gas, or mixtures thereof. Gases that promote damage to the catalyst precursor or mechanical apparatus are preferably avoided.

Certain embodiments employ polar solvents. Suitable polar solvents may include (but are not limited to) $C_1$-$C_3$ alcohols, liquid amines, or polar aprotic solvents such as dimethylformamide (DMF).

In other embodiments, a catalyst precursor is not wetted by polar solvents but is wetted by non-polar solvents. Accordingly, the present invention could be practiced to disperse a compound that attracts a non-polar solvent from the gas phase and then spreads spontaneously in solution on the surface of the non-polar catalyst precursor. Non-polar catalyst precursors might include organic polymers and resins, some forms of elemental carbon including some types of carbon molecular sieves, and some transition metal sulfides. Non-polar solvents include any that are immiscible with water. Non-polar solvents that may be useful include (but are not limited to) volatile hydrocarbons, ethers, halocarbons, halohydrocarbons.

The temperature of the treatment should be low enough such that the solvent is condensed by the promoter salt. This temperature will lie between the freezing point of the solvent and will be slightly higher than its normal boiling point. For example, in the case of $K_2CO_3$, its dihydrate loses water of hydration at 130° C. The maximum temperature at which $K_2CO_3$ could deliquesce must, under those conditions, be below about 130° C. A preferred temperature using water as a solvent is in the range from about 5° C. to about 50° C. Methanol, another solvent that can be used, melts and boils at −94° C. and 65° C., respectively. A preferred temperature using methanol as a solvent is in the range from about −90° C. to about 50° C.

The amount of solvent vapor can vary with the length of time for treatment. A prescribed dispersal could be achieved with less solvent but the dispersal would then probably be slower, as will be appreciated. The optimum amount of solvent required can be established by routine experimentation. Another method to establish the amount of solvent required is to analyze the solvent breakthrough in the carrier gas exiting the bed. Gravimetry and other methods of establishing the solvent load on the catalyst charge can be employed alone or in conjunction with other known methods.

In certain embodiments of the present invention, the pulverized dry solid promoter compound can be potassium carbonate, $K_2CO_3$. Potassium carbonate is substantially deliquescent. In certain embodiments employing $K_2CO_3$ as the promoter, the solvent is water.

Preferred embodiments of the invention minimize the amount of solvent involved in the deposition and distribution of the promoter onto the catalyst. These embodiments can have several advantages. First, the possibility of damage to the catalyst by solvent contact can be minimized. Second, energy that would otherwise be required to remove a larger amount of solvent can be conserved. Third, the methods described herein can be accomplished using simple apparatus and, when dry-mixing is employed, can be conducted within the same equipment that achieves the dry-mixing of the promoter with the catalyst precursor. Fourth, the methods described herein can minimize waste solvent streams. Finally, the promoter can be dispersed before the catalyst is loaded, so that the induction or activation period can be minimized.

Another aspect of the invention provides for use of certain catalyst materials produced, in a reactor for synthesis of alcohols, preferably $C_1$-$C_4$ alcohols, and more preferably substantially ethanol.

The reactor is any apparatus capable of being effective for producing at least one $C_2$-$C_4$ alcohol from syngas. The reactor can be a single vessel or a plurality of vessels. The reactor contains at least one catalyst composition that tends to catalyze the conversion of syngas into $C_2$ and higher alcohols. The "reactor" can actually be a series or network of several reactors in various arrangements. For example, in some variations, the reactor comprises a large number of tubes filled with one or more catalysts as provided herein.

The reactor for converting syngas into alcohols can be engineered and operated in a wide variety of ways. The reactor operation can be continuous, semicontinuous, or batch. Operation that is substantially continuous and at steady state is preferred. The flow pattern can be substantially plug flow, substantially well-mixed, or a flow pattern between these extremes. The flow direction can be vertical-upflow, vertical-downflow, or horizontal. A vertical configuration can be preferred.

In some embodiments, fresh syngas is produced according to methods described in Klepper et al., "METHODS AND APPARATUS FOR PRODUCING SYNGAS," U.S. Patent App. No. 60/948,653 (filed Jul. 9, 2007), which is hereby incorporated by reference herein in its entirety.

Any suitable catalyst or combination of catalysts may be used in a reactor to catalyze reactions converting syngas to alcohols. Suitable catalysts may include, but are not limited to, those disclosed in co-pending and commonly assigned U.S. Patent App. No. 60/948,653. Preferred catalysts minimize the formation of $CO_2$ and $CH_4$ under reaction conditions. Certain catalysts that can be used include Co—Mo—S materials promoted with potassium, which can be delivered (via precursor $K_2CO_3$) as described herein.

In some embodiments, conditions effective for producing alcohols from syngas include a feed hydrogen-carbon monoxide molar ratio ($H_2$/CO) from about 0.2-4.0, preferably about 0.5-2.0, and more preferably about 0.5-1.5. These ratios are indicative of certain embodiments and are not limiting. It is possible to operate at feed $H_2$/CO ratios less than 0.2 as well as greater than 4, including 5, 10, or even higher. It is well-known that high $H_2$/CO ratios can be obtained with extensive steam reforming and/or water-gas shift in operations prior to the syngas-to-alcohol reactor.

In some embodiments, conditions effective for producing alcohols from syngas include reactor temperatures from about 200-400° C., preferably about 250-350° C. Depending on the catalyst chosen, changes to reactor temperature can change conversions, selectivities, and catalyst stability. As is recognized in the art, increasing temperatures can sometimes be used to compensate for reduced catalyst activity over long operating times.

Preferably, the syngas entering the reactor is compressed. Conditions effective for producing alcohols from syngas include reactor pressures from about 20-500 atm, preferably about 50-200 atm or higher. Generally, productivity increases with increasing reactor pressure, and pressures outside of these ranges can be employed with varying effectiveness.

In some embodiments, conditions effective for producing alcohols from syngas include average reactor residence times from about 0.1-10 seconds, preferably about 0.5-2 seconds. "Average reactor residence time" is the mean of the residence-time distribution of the reactor contents under actual operating conditions. Catalyst contact times can also be calculated by a skilled artisan and these times will typically also be in the range of 0.1-10 seconds, although it will be appreciated that it is certainly possible to operate at shorter or longer times.

The catalyst phase can be a packed bed or a fluidized bed. The catalyst particles can be sized and configured such that the chemistry is, in some embodiments, mass-transfer limited or kinetically limited. The catalyst can take the form of a powder, pellets, granules, beads, extrudates, and so on. When a catalyst support is optionally employed, the support may assume any physical form such as pellets, spheres, monolithic channels, etc. The supports may be coprecipitated with active metal species; or the support may be treated with the catalytic metal species and then used as is or formed into the aforementioned shapes; or the support may be formed into the aforementioned shapes and then treated with the catalytic species.

In general, the specific selection of catalyst configuration (geometry), $H_2$/CO ratio, temperature, pressure, and residence time (or feed rate) will be selected to provide, or will be subject to constraints relating to, an economically optimized process. The plurality of reactor variables and other system parameters can be optimized, in whole or in part, by a variety of means. For example, statistical design of experiments can be carried out to efficiently study several variables, or factors, at a time. From these experiments, models can be constructed and used to help understand certain preferred embodiments.

Certain embodiments and aspects of the present invention will now be further described by way of the following examples.

EXAMPLE 1

A catalyst is prepared wherein the catalyst composition comprises Co and Mo, combined with an atomic ratio of Co to Mo of about 0.5. The catalyst composition also comprises sulfur, in an atomic ratio of S to (Co+Mo) of about 2. Potassium is introduced as $K_2CO_3$ so that the atomic ratio of K to (Co+Mo) is about 0.4. Thus 10 g of catalyst powder having a formula $Co_1Mo_2S_6$ is promoted by the addition of 1.9 g of $K_2CO_3$(anhydrous).

This catalyst composition is subject to a method of the invention for dispersal of the promoter onto a solid surface. In this example, $K_2CO_3$ becomes dispersed across the surface of the $Co_1Mo_2S_6$ by 24-hour exposure to $N_2$ saturated with $H_2O$. The $N_2$ saturated with $H_2O$ is prepared by sparging nitrogen through water thermostated at 25° C.

EXAMPLE 2

Surface concentrations of potassium and carbonate were measured by X-ray photoelectron spectroscopy in a series of catalyst samples that had been stored for various lengths of time following the mixing of a transition-metal sulfide powder with a $K_2CO_3$ promoter, as described in Example 1. The areas under the peaks are proportional to the surface concentrations of the respective ions.

FIG. 1 shows the unresolved manifold of the potassium 2p3/2 XPS peak from K+ and the 1s XPS peak from carbon in the form of carbonate. The carbonate 1s line is shifted to higher binding energy compared to reduced carbon, which has a 1s binding energy of about 285 eV or lower. FIG. 1 compares (a) catalyst precursor without $K_2CO_3$; (b, c) catalyst precursor and $K_2CO_3$ recently mixed so that the $K_2CO_3$ is still confined to crystalline particles covering relatively little surface area of the samples; (d) catalyst precursor and $K_2CO_3$ mixed about three months earlier; and (e) catalyst precursor and $K_2CO_3$ mixed six months earlier, so that the $K_2CO_3$ has had time to dissolve (deliquesce) and spread across the catalyst surface. The fraction of the catalyst surface occupied by potassium and carbonate ions is in proportion to the intensity of the combined peaks. Whereas the fraction of surface comprising potassium is low in freshly formulated catalyst samples, that fraction rises progressively with time in storage if container integrity is not complete.

Figure 2:
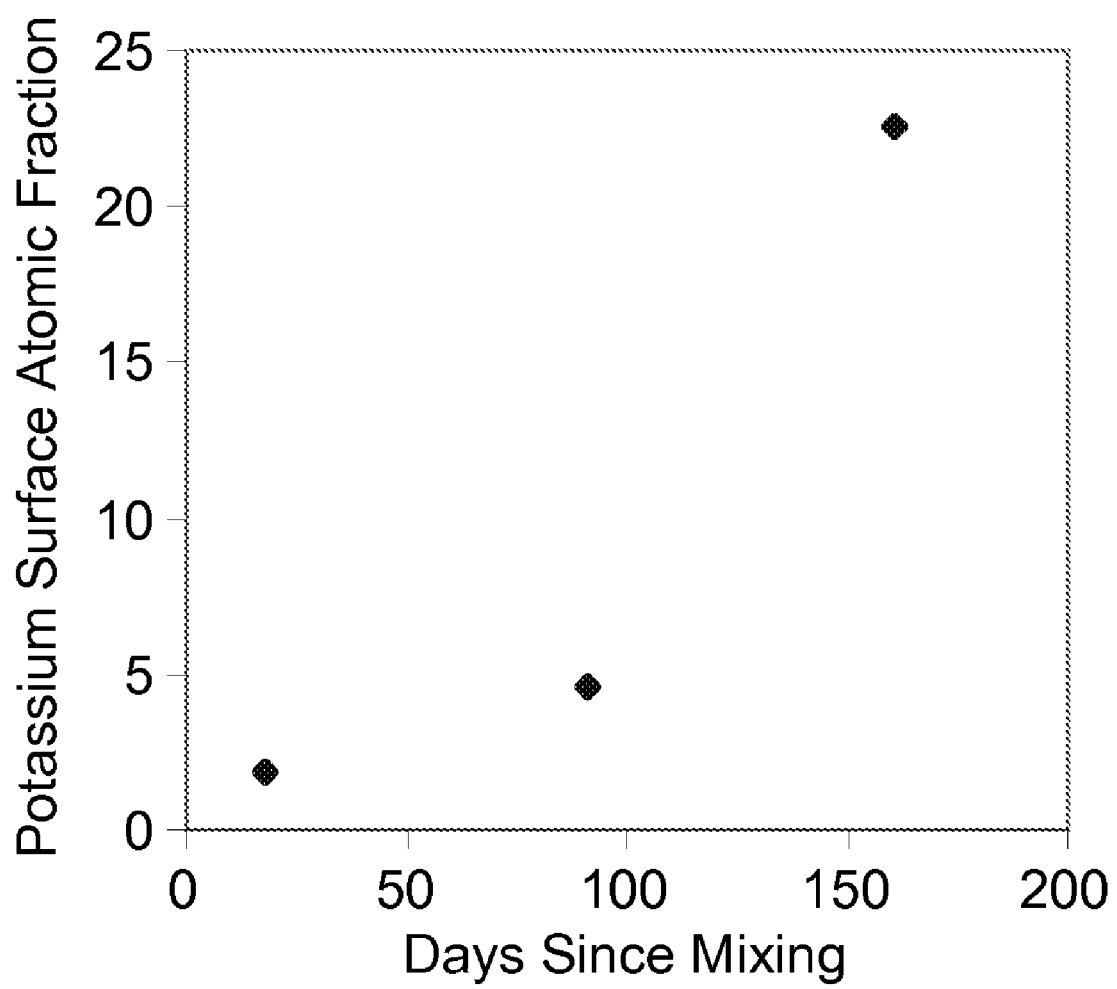
FIG. 2 is an exemplary graph depicting the rising surface concentration of a deliquesced promoter over time, wherein the promoter is potassium, the solvent is water, and the gas is air.

FIG. 2 shows how the surface concentration of potassium rose with time as mixtures of catalyst precursor with $K_2CO_3$ were held in storage and absorbed increasing amounts of moisture (solvent=$H_2O$) from the air. The samples were initially prepared with the same bulk mass fractions of $K_2CO_3$ (anhydrous). This mass fraction was 15 wt %. The graph presents XPS surface elemental analyses indicating that the surface fraction of potassium increased with time while the samples were stored in containers that did not prevent the penetration of moist ambient air.

Figure 3:
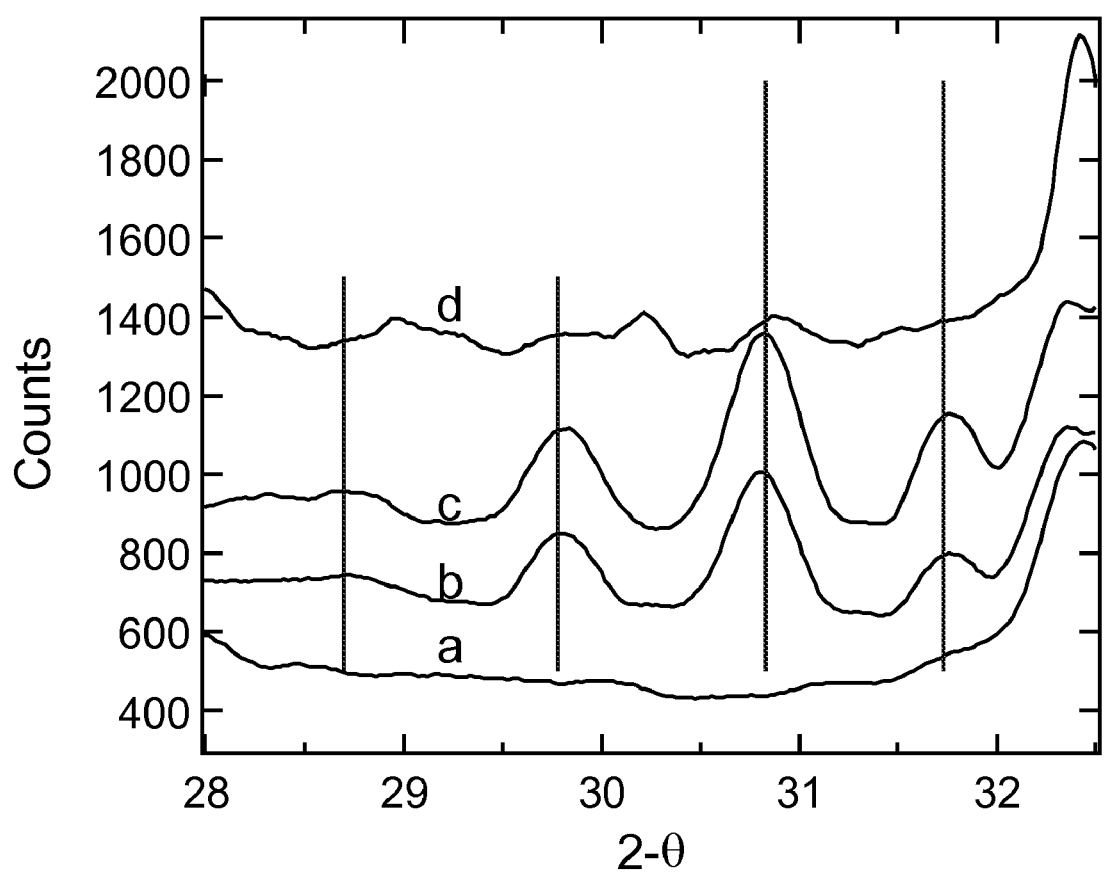
FIG. 3 shows XRD measurements that demonstrate the effectiveness of certain embodiments of the invention.

In other measurements using the X-ray diffraction technique, it was observed that the same samples that had been in extended storage no longer showed the diffraction peaks that are characteristic of the mechanically pulverized $K_2CO_3$, which diffraction peaks are apparent in the X-ray diffraction patterns of recently formulated (dry-mixed) catalyst samples. This observation is shown in FIG. 3. The X-ray diffraction patterns were measured using Cu Kα radiation, taking 0.02° 2θ between data points. Trace (a) is from the diffraction pattern of catalyst precursor without $K_2CO_3$. Patterns (b) and (c) describe catalyst that was mixed with $K_2CO_3$ about a month before the measurements. Trace (d) describes catalyst that was mixed with $K_2CO_3$ about six months before the measurement. The diffraction lines characteristic of the carbonate phase are almost absent from trace (d). The marked diffraction lines are not due to the catalyst precursor but rather are an index for the promoter phase $K_4H_2(CO_3)_3 \cdot 1.5H_2O$, indicating that the $K_2CO_3$ (anhydrous) passed through other phases in the process of hydration.

The use of X-ray diffraction to monitor dispersal of deliquescent compounds over refractory oxides was previously reported by Zong et al., "Dispersion State and Dispersion Capacity of $AlCl_3$ and $FeCl_3$ on γ-$Al_2O_3$ Surface," *Cuihua Xuebao* 18, 321-323 (1997).

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A method for dispersal of a promoter onto a solid surface, said method comprising:
   (i) providing a catalyst material comprising a solid surface that is at least partially hydrophilic;
   (ii) providing a deliquescent material comprising, in free or combined form, a promoter;
   (iii) mixing said catalyst material and said deliquescent material, thereby creating a mixture; and
   (iv) contacting said mixture with a gas phase comprising a solvent, under conditions effective for deliquescence, whereby said promoter is dispersed onto said solid surface.

2. The method of claim 1, wherein said solvent is polar.

3. The method of claim 2, wherein said solvent is water.

4. The method of claim 2, wherein said solvent is selected from the group consisting of $C_1$-$C_3$ alcohols, liquid amines, and polar aprotic solvents.

5. The method of claim 4, wherein said solvent is DMF.

6. The method of claim 1, wherein said solvent is non-polar.

7. The method of claim 6, wherein said non-polar solvent is selected from the group consisting of hydrocarbons, ethers, and halocarbons.

8. The method of claim 1, wherein said gas phase comprises an inert gas.

9. The method of claim 1, wherein said gas phase comprises air.

10. A method for dispersal of a promoter onto a solid surface, said method comprising:
   (i) providing a catalyst material comprising a solid surface that is at least partially hydrophilic;
   (ii) providing a deliquescent material comprising, in free or combined form, a promoter;
   (iii) mixing said catalyst material and said deliquescent material, thereby creating a mixture; and (iv) contacting said mixture with a gas phase comprising a solvent, under conditions effective for deliquescence and at a temperature such that said solvent is condensable, whereby said promoter is dispersed onto said solid surface.

11. The method of claim 1 or 10, wherein said deliquescent material is $K_2CO_3$ and said promoter is potassium.

12. The method of claim 1, wherein said catalyst material comprises a non-polar material selected from the group consisting of organic polymers, elemental carbon, and transition metal sulfides.

13. The method of claim 1, wherein said solid surface has catalytic activity, and said promoter enhances said catalytic activity.

14. The method of claim 13, wherein said catalytic activity causes the conversion of syngas into a mixture comprising one or more $C_1$-$C_4$ alcohols.

15. The method of claim 14, wherein said catalyst material comprises cobalt, molybdenum, and sulfur.

16. The method of claim 1 or 10, wherein said promoter dispersal is substantially uniform.

17. The method of claim 1, further comprising the step of loading a material or mixture obtained from any of steps (i)-(iv) into a reactor.

18. The method of claim 17, wherein the promoter is dispersed before the catalyst is loaded into said reactor.

19. The method of claim 1, further comprising use of the promoted catalyst for the conversion of syngas into at least one $C_1$-$C_4$ alcohol.

20. The method of claim 19, wherein at least one of said $C_1$-$C_4$ alcohols is ethanol.

21. A method for producing at least one $C_1$-$C_4$ alcohol, said method comprising
  (i) providing a catalyst material comprising a solid surface that is at least partially hydrophilic;
  (ii) providing a deliquescent material comprising, in free or combined form, a promoter;
  (iii) mixing said catalyst material and said deliquescent material, thereby creating a mixture;
  (iv) contacting said mixture with a gas phase comprising a solvent, under conditions effective for deliquescence, whereby said promoter is dispersed onto said solid surface, thereby generating a promoted catalyst; and
  (v) contacting said promoted catalyst with syngas to produce at least one $C_1$-$C_4$ alcohol.

22. The method of claim 21, wherein at least one of said $C_1$-$C_4$ alcohols is ethanol.

* * * * *